US007012069B2

(12) United States Patent
Song et al.

(10) Patent No.: US 7,012,069 B2
(45) Date of Patent: Mar. 14, 2006

(54) LIVER X RECEPTOR AGONISTS

(75) Inventors: Ching Song, Chicago, IL (US); Shutsung Liao, Chicago, IL (US)

(73) Assignee: ARCH Development Corporation, Chicago, IL (US)

( * ) Notice: Subject to any disclaimer, the term of this patent is extended or adjusted under 35 U.S.C. 154(b) by 0 days.

(21) Appl. No.: 10/137,695

(22) Filed: May 2, 2002

(65) Prior Publication Data

US 2002/0193357 A1 Dec. 19, 2002

Related U.S. Application Data

(60) Provisional application No. 60/288,643, filed on May 3, 2001.

(51) Int. Cl.
*A61K 31/56* (2006.01)
*C07J 9/00* (2006.01)

(52) U.S. Cl. ...................... 514/182; 552/542
(58) Field of Classification Search ........... 552/542; 514/182
See application file for complete search history.

(56) References Cited

U.S. PATENT DOCUMENTS 5,332,851 A 7/1994 Kumai et al.

FOREIGN PATENT DOCUMENTS

CN 110729 * 3/1995
CN 123286388 3/1995

OTHER PUBLICATIONS

Charles Freudenreich, et al., "Design of Inhibitors from the Three–Dimensional Structure of Alcohol Dehydrogenase, Chemical Synthesis and Enzymatic Properties", *J. Am. Chem. Soc.*, pp. 3344–3353, (1984).
Bethany A. Janowski, et al., "Structural requirements of ligands for the oxysterol liver X receptors LXRa and LXRb", *Proc. Natl. Acad. Sci., USA*, vol. 96, pp. 266–271, (Jan. 1999).
Bryan A. Laffitte, et al., "LXRs control lipid–inducible expression of the apolipoprotein E gene in macrophages and adipocytes", *PNAS*, vol. 98, pp. 507–512, (Jun. 16, 2001).
Yvonne Lange, et al., "Cholesterol Movement in Niemann–Pick Type C Cells and in Cells Treated with Amphiphiles", *The Journal of Biological Chemistry*, vol. 275, No. 23, pp. 17468–17475, (Jun. 9, 2000).
Cohen–Solal et al., "Effects of hyodeoxycholic acid and alpha–hyocholic acid, two 6 alpha–hydroxylated bile acids, on cholesterol and bile acid metabolism in the hamster", *Biochimica et biophysica Acta*, 1257:189–197 (1995).
English language translation of Kuritzkes et al., "3–epi–Uzarigenin and 3–epa–17α–Uzarigenin", *Helvetica Chimica Acta*, 14:1502–1515 (1959).

English language translation of Polonia et al., "Die Konstitution des Xysmalogenins", *Helvetica Chimica Acta*, 11:1437–1446 (1959).
English language translation of Tamm et al., "Umwandlung von Cardenoliden durch Mikroorganismen. III. Umsetzung von Aglykonen und Glykosiden mit Fusarium lini", *Helvetica Chimica Acta*, 21: 239–259 (1959).
English language translation of Tschesche et al., "Uber pflanzliche Herzgifte, XIX. Mitteil., Die Glykoside der Uzara–Wurzel", *Chemische Berichte*, $85^{th}$ vol., No. 11:1042–1053 (1952).
McKee et al., "HIV–Inhibitory Natural Products. 11. Comparitive Studies of Sulfated Sterols from Marine Invertebrates", *J. Med. Chem.*, 37:793–797 (1994).
Riccio et al., "Unusual Sulfated Marine Steroids from the Ophiuroid *Ophioderma Longicaudum*", *Tetrahedron*, 41(24):6041–6046 (1985).

* cited by examiner

*Primary Examiner*—Barbara P. Badio
(74) *Attorney, Agent, or Firm*—Fish & Richardson P.C.

(57) ABSTRACT

A compound of formula (I):

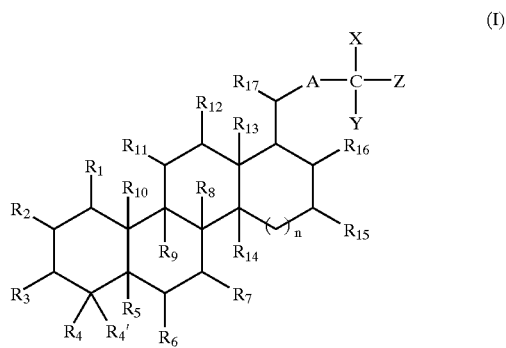

Each of $R_1$, $R_2$, $R_3$, $R_4$, $R_{4'}$, $R_5$, $R_6$, $R_7$, $R_{11}$, $R_{12}$, $R_{15}$, $R_{16}$, and $R_{17}$, independently, is hydrogen, halo, alkyl, haloalkyl, hydroxy, amino, carboxyl, oxo, sulfonic acid, or alkyl that is optionally inserted with —NH—, —N(alkyl)—, —O—, —S—, —SO—, —$SO_2$—, —O—$SO_2$—, —$SO_2$—O—, —$SO_3$—O—, —CO—, —CO—O—, —O—CO—, —CO—NR'—, or —NR'—CO—; or $R_3$ and $R_4$ together, $R_4$ and $R_5$ together, $R_5$ and $R_6$ together, or $R_6$ and $R_7$ together are eliminated so that a C=C bond is formed between the carbons to which they are attached; each of $R_8$, $R_9$, $R_{10}$, $R_{13}$, and $R_{14}$, independently, is hydrogen, halo, alkyl, haloalkyl, hydroxyalkyl, alkoxy, hydroxy, or amino; n is 0, 1, or 2; A is alkylene, alkenylene, or alkynylene; and each of X, Y, and Z, independently, is alkyl, haloalkyl, —OR', —SR', —NR'R", —N(OR')R", or —N(SR')R"; or X and Y together are =O, =S, or =NR'; wherein each of R' and R", independently, is hydrogen, alkyl, or haloalkyl.

8 Claims, No Drawings

LIVER X RECEPTOR AGONISTS

CROSS REFERENCE TO RELATED APPLICATION

Pursuant to 35 U.S.C. §119(e), this application claims the benefit of prior U.S. provisional application 60/288,643, filed May 3, 2001.

FUNDING

Work described herein was supported by grants from the National Institute of Health (CA-58073 and DK-41670). The U.S. government has certain rights in the invention.

BACKGROUND OF THE INVENTION

Liver X receptors (LXRs), members of the nuclear receptor super-family, include LXRα and Ubiquitous Receptor (UR, also called LXRβ). They transactivate gene expression. Several cholesterol homeostasis-related genes have been identified as LXR direct targets, e.g., those coding for cholesterol efflux transporter ATP-binding cassette 1 ABCA1 and ABCG1, cholesterol 7α-hydroxylase (the rate-limiting enzyme for bile acid synthesis from cholesterol), cholesteryl ester transfer protein (CETP), lipoprotein Apolipoprotein E (ApoE), and sterol regulatory element-binding protein 1c (SREBP-1c). See, e.g., Schwartz et al., *Biochem. Biophys. Res. Commun.*, 2000, 274: 794–802; Laffitte et al., *Proc. Natl. Acad. Sci. USA*, 2001, 98(2): 507–512; and Repa et al., *Genes Dev.*, 2000, 14: 2819-30.

Regulation of these genes by LXRs affects cholesterol reverse transport and disposal, which in term has a direct impact on the formation of lipids and fibrous elements, expression of ApoE gene, and activation of nuclear factors kappa-B and AP-1. Accumulation of lipids and fibrous elements in arteries results in atherosclerosis, the underlying cause of various diseases such as heart disease and stroke. Deficiency of ApoE gene expression has been found related to diseases such as Alzheimer's disease. Activation of nuclear factors kappa-B and AP-1 modulates the human immune system and enhance its anti-inflammatory abilities.

SUMMARY OF THE INVENTION

The present invention is based on the discovery of novel steroid compounds that function as LXRs agonists.

One aspect of this invention relates to compounds of formula (I):

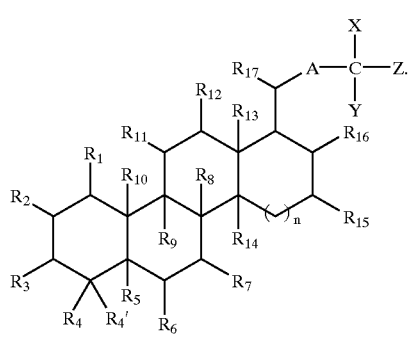

(I)

Each of $R_1$, $R_2$, $R_3$, $R_4$, $R_{4'}$, $R_5$, $R_6$, $R_7$, $R_{11}$, $R_{12}$, $R_{15}$, $R_{16}$, and $R_{17}$, independently, is hydrogen, halo, alkyl, haloalkyl, hydroxy, amino, carboxyl, oxo, sulfonic acid, or alkyl that is by optionally inserted with —NH—, —N(alkyl)-, —O—, —S—, —SO—, —SO$_2$—, —O—SO$_2$—, —SO$_2$—O—, —SO$_3$—O—, —CO—, —CO—O—, —O—CO—, —CO—NR'—, or —NR'—CO—; or $R_3$ and $R_4$ together, $R_4$ and $R_5$ together, $R_5$ and $R_6$ together, or $R_6$ and $R_7$ together are eliminated so that a C=C bond is formed between the two carbons to which they are attached; each of $R_8$, $R_9$, $R_{10}$, $R_{13}$, and $R_{14}$, independently, is hydrogen, halo, alkyl, haloalkyl, hydroxyalkyl, alkoxy, hydroxy, or amino; n is 0, 1, or 2; A is alkylene, alkenylene, or alkynylene; and each of X, Y, and Z, independently, is alkyl, haloalkyl, —OR', —SR', —NR'R", —N(OR')R", or —N(SR')R"; or X and Y together are =O, =S, or =NR'; each of R' and R", independently, being hydrogen, alkyl, or haloalkyl.

The terms "alkyl," the prefix "alk" (e.g., as in alkoxy), and the suffix "-alkyl" (e.g., as in hydroxyalkyl) mentioned above all refer to $C_{1-18}$ linear or branched.

Referring to formula (I), one subset of the compounds is featured by that each of $R_5$ and $R_6$, independently, is hydrogen, alkyl, haloalkyl, hydroxy, or amino; and another subset is featured by that $R_5$ and $R_6$ together are eliminated so that a C=C bond is formed between the two carbons to which $R_5$ and $R_6$ are attached. Two other subsets of the compounds are respectively featured by that X and Y together are =O or =S, and Z is —OR', —SR', —NR'R", —N(OR')R", or —N(SR')R"; and that each of X, Y, and Z, independently, is alkyl, haloalkyl, —OR', —SR', —NR'R", —N(OR')R", or —N(SR')R".

The compounds described above also include their salts and prodrugs, if applicable. Such salts, for example, can be formed between a positively charged substituent in a compound of this invention (e.g., amino) and an anion. Suitable anions include, but are not limited to, chloride, bromide, iodide, sulfate, nitrate, phosphate, citrate, methanesulfonate, trifluoroacetate, and acetate. Likewise, a negatively charged substituent in a compound of this invention (e.g., carboxylate) can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing steroid compounds described above.

Another aspect of this invention relates to a pharmaceutical composition including an effective amount of a compound of this invention and a pharmaceutically acceptable carrier. Indeed, the compounds of this invention can be used to treat an LXR-mediated disease such as heart disease and stroke, Alzheimer's disease, and an inflammatory disorder. Thus, also within the scope of this invention are a method of using a compound of this invention to treat one of these diseases; and a method of using such a compound to manufacture a medicament used in treating one of the just-mentioned diseases.

Details of several compounds of this invention are set forth in the accompanying description below. Other features, objects, and advantages of this invention will be apparent from the description and from the claims.

DETAILED DESCRIPTION OF THE INVENTION

Compounds of this invention can be synthesized by methods well known in the art by using a suitable steroid as a starting material. More specifically, such a steroid possesses a substitutent at C-17 [the carbon to which $R_{17}$ is attached, see formula (I) above] that can be modified to contain a moiety defined by X, Y, and Z [also shown in formula (I)]. Examples include cholic acid, dehydrocholic acid, deoxycholic acid, lithocholic acid, ursodeoxycholic acid, hyocholic acid, hyodeoxycholic acid, and cholanoic acid. They are either commercially available or can be synthesized by methods described in the literature, e.g., Roda et al., *F. Lipid Res.,* 1994, 35: 2268–2279; and Roda et al., *Dig. Dis. Sci.,* 1987, 34: 24S-35S.

A compound of this invention that has an amide-containing substitutent at C-17 (i.e., X and Y together are =O, and Z is amine) can be prepared by reacting a steroid having a carboxyl-containing substituent at C-17 with an amino-containing compound (such as dimethylamine, aniline, glycine, and phenylalanine). Similarly, a compound of this invention that has an ester-containing substitutent at C-17 (i.e., X and Y together are =O, and Z is alkoxy) can be prepared by reacting a steroid having a carboxyl-containing substituent at C-17 with a hydroxyl-containing compound (such as ethanol and isopropanol). The amide- or ester-forming reaction can take place in any suitable solvents. If the reaction takes place in an aqueous solution, isolation of the steroid product for in vitro or in vivo screening assays may not be necessary.

A compound of this invention that has a carbonyl-containing substitutent at C-17 (i.e., X and Y together are =O) can be converted, e.g., to a thiocarbonyl-containing compound of this invention (i.e., X and Y together are =S) by reacting it with sulfur hydride, or to an imino-containing compound of this invention (i.e., X and Y together are =NR) by reacting it with hydrazine. See Janssen et al. (Ed.), Organosulfur Chemistry; Wiley: New York, 1967, 219–240; and Patai et al. (Ed.), The Chemistry of the Carbon-Nitrogen Double Bond; Wiley: New York, 1970, 64–83 and 465–504, respectively.

Substituents at ring atoms other than C-17, if necessary, can further be modified by methods well known in the art. For instance, a hydroxyl substituent at C-3 can be converted to an ester substituent by reacting it with an acid such as acetic acid.

Due to the simplicity of the reaction, it can be easily automated. Isolation and quantification of the product can be done by thin-layer chromatography, high pressure liquid chromatography, gas chromatography, capillary electrophoresis, or other analytical and preparative procedures.

A compound that does not contain a carbonyl, thiocarbonyl, or imino group in the C-17 substituent can also be prepared by methods well known in the art. For instance, 3α,6α,24-trihydroxy-24,24-di(trifluoromethyl)-5β-cholane can be prepared according to the following scheme:

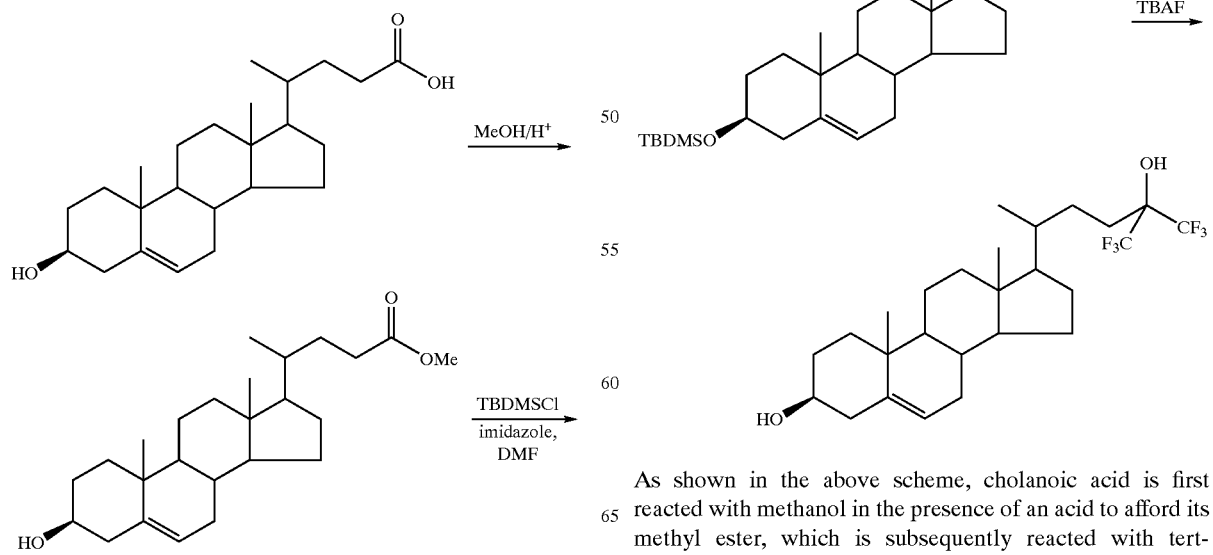

As shown in the above scheme, cholanoic acid is first reacted with methanol in the presence of an acid to afford its methyl ester, which is subsequently reacted with tert-butyldimethylsilyl chloride (TBDMSCl) for protection of the 3β-hydroxyl group. The protected methyl ester is then converted to an aldehyde by reacting with di(iso-butryl) alumina hydride, which is subsequently converted to an alcohol, α-substituted with trifluoromethyl, by reacting with trimethyl(trifluoromethyl)silane. The alcohol then undergoes the Dess-Martin reaction for conversion to a ketone. See Dess et al., J. Org. Chem., 1983, 38: 4155. The ketone is treated with trimethyl(trifluoromethyl)silane again to afford an alcohol, α-substituted with two trifluoromethyl groups. Finally, the disubstituted alcohol is deprotected by reacting it with tetrabutylammonium fluoride (TBAF) to afford 3α,6α,24-trihydroxy-24,24-di(trifluoromethyl)-5β-cholane.

An effective amount of a compound thus prepared can be formulated with a pharmaceutically acceptable carrier to form a pharmaceutical composition before being administered for treatment of a disease related to atherloscerlosis or ApoE deficiency, or an inflammatory disease. "An effective amount" refers to the amount of the compound which is required to confer therapeutic effect on the treated subject. The interrelationship of dosages for animals and humans (based on milligrams per square meter of body surface) is described by Freireich et al., Cancer Chemother. Rep. 1966, 50, 219. Body surface area may be approximately determined from height and weight of the patient. See, e.g., Scientific Tables, Geigy Pharmaceuticals, Ardley, N.Y., 1970, 537. Effective doses will also vary, as recognized by those skilled in the art, depending on the route of administration, the excipient usage, and the optional co-usage with other therapeutic treatments. Examples of pharmaceutically acceptable carriers include colloidal silicon dioxide, magnesium stearate, cellulose, sodium lauryl sulfate, and D&C Yellow #10.

The pharmaceutical composition may be administered via a parenteral route, e.g., topically, intraperitoneally, and intravenously. Examples of parenteral dosage forms include an active compound dissolved in a phosphate buffer solution, or admixed with any other pharmaceutically acceptable carrier. Solubilizing agents, such as cyclodextrins, or other solubilizing agents well known to those familiar with the art, can also be included in the pharmaceutical composition.

An in vitro assay can be conducted to preliminarily screen a compound of this invention for its efficacy in agonizing LXRs and thus in treating an LXR-mediated disease. For instance, kidney cells are transfected with a luciferase reporter gene (which includes a human c-fos minimal promoter) and an LXR. After incubating the transfected cells with a compound to be tested, the activity of luciferase is measured to determine the transactivation extent of the reporter gene.

Compounds that show efficacy in the preliminary assay can be further evaluated in an animal study by a method also well known in the art. For example, a compound can be orally administered to mice fed with a cholesterol-containing diet. The efficacy of the compound can be determined by comparing cholesterol levels in various tissues of the treated mice with those in non-treated mice.

Without further elaboration, it is believed that one skilled in the art, based on the description herein, can utilize the present invention to its fullest extent. All publications recited herein are hereby incorporated by reference in their entirety. The following specific examples, which describe synthesis and biological testing of several compounds of this invention, are therefore to be construed as merely illustrative, and not limitative of the remainder of the disclosure in any way whatsoever.

EAXMPLE 1

Synthesis of Compounds of This Invention

3α,6α,24-trihydroxy-24,24-di(trifluoromethyl)-5β-cholane [Compound (1)] was synthesized by the method described above.

3α,6α-dihydroxy-5β-cholanoic acid-N-methyl-N-methoxy-24-amide [Compound (2)], 2,2,2-trifluoroethyl-3α,6α-dihydroxy-5β-cholanoic acid 24-amide [Compound (3)], 24-cholesten-amide [Compound (4)], N,N-dimethyl-24-cholesten-amide [Compound (5)], and N-methoxy-24-cholesten-amide [Compound (6)] were synthesized by the following method:

A steroid 24-carboxylic acid (Sigma, St. Louis, Mo.), an amine, diethyl cyanophosphonate (Aldrich, Milwaukee, Wis.), and triethylamine were dissolved in dimethylformamide. The solution was stirred at 20–70° C. for 12–16 hours, quenched with ice, and then extracted with ethyl acetate. The ethyl acetate extract thus obtained was washed subsequently with a 1.0 N HCl solution and with a 1.0 N NaOH solution, and then dried over anhydrous sodium sulfate. The crude product was obtained after removal of ethyl acetate and was purified using standard silica chromatography if necessary.

EXAMPLE 2

Reporter Gene Transactivation Assay

Human embryonic kidney 293 cells were seeded into a 48-well culture plate at 105 cells per well in a Dulbecco's modified Eagle's medium (DMEM) supplemented with 10% fetal bovine serum. After incubation for 24 hours, the cells were transfected by the calcium phosphate coprecipitation method with 250 ng of a pGL3/UREluc reporter gene that consisted of three copies of AGGTCAagccAGGTCA fused to nucleotides −56 to +109 of the human c-fos promoter in front of the firefly luciferase gene in the plasmid basic pGL3 (Promega, Madison, Wis.), 40 ng pSG5/hRXR$_\alpha$, 40 ng pSG5/rUR or CMX/hLYRα, 10 ng pSG5/hGrip1, 0.4 ng CMV/R-luc (transfection normalization reporter, Promega) and 250 ng carrier DNA per well. After incubation for another 12 to 24 hours, the cells were washed with phosphate buffer saline and then refed with DMEM supplemented with 4% delipidated fetal bovine serum. An ethanol solution containing a compound to be tested, i.e., Compounds (2) or (3), was added in duplicate to the DMEM cell culture with the final concentration of the compound of 1 to 10 $\mu$M and the final ethanol concentration of 0.2%. After incubation for another 24 to 48 hours, the cells were harvested and the luciferase activity was measured with a commercial kit (Promega Dual luciferase II) on a Monolight luminometer (Becton Dickenson, Mountain View, Calif.).

The results show that both Compound (2) and Compound (3) were potent agonists of LXRα and UR.

EXAMPLE 3

Effect on Diet-Induced Hypercholesterolemic Mice

Two groups of 3-month old Non-Swiss Albino mice (Harlan, Indianapolis, Ind.), i.e., a control group and a treatment group, were fed with a chow diet (Harlan Teklad 7001), (Harlan, Indianapolis, Ind.) supplemented with 1% cholesterol, for 7 days. The control group received drinking water containing 0.25% hydroxypropyl-β-cyclodextrin (HPCD, Acros Organic, Somerville, N.J.), while the treatment group received drinking water containing both 0.25% HPCD and Compound (2) (0.125, 0.25 and 0.5 g/L). The mice had free access to the chow diet and the drinking water. Water consumption in the control and treatment groups differed by less than 10%.

Blood was collected from 4 hours fasted mice. The levels of serum cholesterol and triglycerides were enzymatically measured with a commercial kit (Sigma, St. Louis, Mo.). High-density lipoprotein cholesterol was isolated and enzymatically quantified by methods described in Warnick et al., Clin. Chem. 1982, 28: 1379–88. Liver cholesterol and triglycerides were isolated and quantified by methods described in Bligh et al., Canadian J. Biochem. Physiol. 1959, 37:911–918. Fecal bile acids were reduced with sodium borohydride, and then extracted and quantified by methods described in Turley et al., J. Cardiovasc. Pharmacol. 1996, 27: 71–79. Bile acids were quantified using a commercial kit (Sigma, St. Louis, Mo.).

The results show that cholesterol feeding did not change the circulating cholesterol levels, but increased the liver cholesterol levels in mice. The administration of Compound (2) prevented the liver cholesterol levels from increasing, and accelerated cholesterol removal by increasing fecal bile acid secretion. The levels of triglycerides in serum and liver were not affected by the administration of Compound (2).

Male C57BL/6J mice (Jackson Laboratory, Bar Harbor, Me.), which are susceptible to development of atherosclerosis, were used for the same study. The serum cholesterol levels were lowered in a Compound (2) dose-dependent manner, while the serum triglycerides levels did not significantly increase throughout the entirely study period.

EXAMPLE 4
Effect on Diet-Induced Hypercholesterolemic Hamsters

The bile acid and circulating cholesterol profiles of hamsters, but not rats or mice, are similar to those of humans. In addition, the major cholesterol carrier in human and hamster serum is low-density lipoprotein, compared to high-density lipoprotein in rats and mice. Hamsters were therefore used to evaluate the effect of Compound (2) on cholesterol and triglyceride profiles.

Compound (2) was orally administered to hamsters that were fed with a regular chow diet at doses up to 200 mg/kg/day for 2 weeks. The levels of serum cholesterol or triglycerides in the hamster did not change. On the other hand, when Compound (was administered to hamsters fed with a chow diet supplemented with 1% cholesterol, it prevented the level of serum cholesterol or cholesteryl ester in liver from increasing. The serum triglyceride levels in hamsters administered with Compound (2) was significantly higher than that in the vehicle-treated kamsters. They were however about the same in the control animals fed with a regular chow diet and were within the normal range as reported in Trautwein et al., Comp. Biochem. Physiol. A Mol. Integ. Physiol. 1999, 124: 93–103. The decrease of triglyceride levels in the hamsters in the vehicle-treated group was probably due to the massive accumulation of cholesteryl esters in the liver.

EXAMPLE 5
Effect on Diet-Induced Hypercholesterolemic Rats

An animal study was conducted by the method described in Example 4, except that Compound (3) and male 3-month old Harlan Sprague-Dawley rats (Harlan, Indianapolis, Ind.) were used, instead of Compound (2) and hamsters. The results show that Compound (3), like Compound (2), also had a hypocholesterolemic effect.

EXAMPLE 6
In Vitro Study of the Effect on ApoE Gene Expression (1) In Rat Astrocytes Astrocyte cultures were prepared from the cerebral cortex of 1–2-day-old Harlan Sprague-Dawley neonatal rats rats (Harlan, Indianapolis, Ind.) by a method described in LaDu et al., *J. Biol. Chem.*, 2000, 275 (43): 33974–80. The astrocyte cells were grown to 90% confluency before the initiation of experiments. The culture medium was changed to α-minimum essential medium containing N2 supplements (Life Technologies, Inc., Gaithersburg, Md.), to which Compound (2) (0.1 to 1 μM/L) was added in triplicates. After incubation for 48–72 hours, a conditioned medium was collected and mixed with a SDS loading buffer. Cells lysate was made in situ by adding a SDS loading buffer to the culture plates.

Western blot analysis was performed as described by LaDu et al., supra. Cell lysate and conditioned media were loaded on a 4–20% gradient SDS-polyacrylamide electrophoresis gel and transferred onto nitrocellulose membranes after electrophoresis. The membrane were stained with amino black briefly and de-stained in distilled water. After the protein staining patterns were scanned, the membranes were blocked with a phosphate-buffered saline solution containing 0.2% Tween 20 and 1% fat-free milk powder. The ApoE amount was detected by using anti-rat ApoE polyclonal antibodies, horseradish peroxidase-conjugated goat anti-rabbit IgG, a chmiliminescent substrate (Pierce, Rockford, Ill.) and X-ray films.

Compared with vehicle treatment, administration of Compound (2) resulted in an increase in the amount of ApoE in both cell medium and lysate.

(2) In Human THP-1 Cells

THP-1 cells (ATCC, Manassas, Va.), a human monocytic cell line, were used in an in vitro study by the method described in Example 6. More specifically, they were maintained in an RPMI1640 medium which contained 10% fetal bovine serum, and then activated for 24 hours by treating with PMA before use. The medium was then replaced with a serum-free Cellgro™ complete medium (Mediatech, Fisher Scientific, Pittsburgh, Pa.). An ethanol solution containing Compound (2) (0.1 to 1 μM/L) was then added to the cell medium. The cells were incubated for another 48–72 hours and harvested. The ApoE amounts in the cells were determined by the method described above.

The results show that administration of Compound (2) also resulted in an increase in the amount of both secreted and cell associated ApoE.

EXAMPLE 7
Animal Study of ApoE Gene Expression

Twenty 4-month old male C57BL/6J mice (Jackson Laboratory, Bar Harbor, Me.) were fed for 8 weeks with a chow diet (Harlan 7001) (Harlan, Indianapolis, Ind.) which was supplemented with 1.25% cholesterol, 0.5% cholic acid, and 15% corn oil. Three groups, 5 mice each, received drinking water containing 0.25% HPCD and Compound (2 at various concentrations, so that they have calculated doses of 25, 50 and 100 mg/kg body weight/day, respectively. The fourth group received no Compound (2). At the end of the 8 weeks, the mice were sacrificed and their brains were collected. ApoE mRNA from pooled brains of each group was isolated using a phenol-containing reagent (Trizol™ reagent, Life Technologies, Gaithersburg, Md.). The mRNA was analyzed by Northern blot analysis to determine the extent of ApoE gene expression.

The results show that more ApoE mRNA was detected in the treatment group than that in the vehicle group. Treatment with Compound (2) decreased total cholesterol levels in circulation and suppressed cholesterol accumulation in liver.

EXAMPLE 8
Animal Study of ApoE Gene Expression

Twenty LDL receptor null gene mice were fed with an atherogenic diet (15% fat, 0.2% cholesterol) and divided into 4 groups (5 each) for receiving, respectively, 0 (control), 25, 50, and 100 mg/kg body weight/day of Compound (2) dissolved in their drinking water which also contained 0.25% HPCD, for 2 weeks. At the end of the 2 weeks, the mice were sacrificed and various tissues (i.e., liver, brain, and intestine) were collected. The collected tissues were analyzed by the method described in Example 7.

The results show that the treatment groups had a total serum cholesterol level of 700 mg/dL, compared to 1400 mg/dL in the control group. The amount of ApoE mRNA in the brains of treated mice was 4 to 5 times higher than that in the control group. In situ hybridization using anti-ApoE probe showed more mRNA in the brains of the treated mice than that in the untreated mice, especially in the region of hippocampus and cerebral cortex.

EXAMPLE 9
Animal Study of Anti-Inflammatory Effect

This study was conducted according to a method described in Tonelli et al., Endocrinology 1965, 77: 625–634. A croton oil mixture was prepared to contain 1% croton oil, 25% pyridine, 60% ethyl ether, 5% water and a compound to be tested, i.e., Compounds (4) and (6). Non-swiss Albino male mice Harlan (Indianapolis, Ind.) were used.

The right ear of each mouse was applied topically with 100 mL of croton oil mixture on both sides. Six hours later ears were cut off and their weight were measured. It was found that weight gains of the ears treated with Compound (4) or Compound (6) were significantly less than those of the ears treated with croton oil only. Thus, these compounds are efficacious anti-inflammatory agents.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A compound of formula (I):

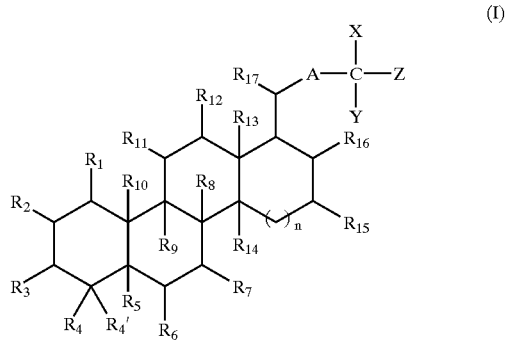

in which each of $R_1$, $R_2$, $R_4$, $R_{4'}$, $R_5$, $R_7$, $R_{11}$, $R_{12}$, $R_{15}$, $R_{16}$, and $R_{17}$, independently, is hydrogen, halo, alkyl, haloalkyl, hydroxy, amino, carboxyl, oxo, sulfonic acid, or alkyl that is optionally inserted with —NH—, —N(alky)-, —O—, —S—, —SO—, —SO$_2$—, —O—SO$_2$—, —SO—O—, —SO$_3$—O—, —CO—, —CO—O—, —O—CO—, —CO—NR'—, or —NR'—CO—;

each of $R_3$ and $R_6$ is hydroxy;

each of $R_8$, $R_9$, $R_{10}$, $R_{13}$, and $R_{14}$, independently, is hydrogen, halo, alkyl, haloalkyl, hydroxyalkyl, alkoxy, hydroxy, or amino;

n is 0, 1, or 2;

A is alkylene, alkenylene, or alkynylene; and one of X, Y, and Z is —OR', and the other two are haloalkyl;

wherein R' is hydrogen.

2. The compound of claim 1, wherein $R_5$ is hydrogen, alkyl, haloalkyl, hydroxy, or amino.

3. The compound of claim 2, wherein $R_5$ is H.

4. The compound of claim 1, wherein each of $R_1$, $R_2$, $R_4$, $R_{4'}$, $R_7$, $R_8$, $R_9$, $R_{11}$, $R_{12}$, $R_{14}$, $R_{15}$, $R_{16}$, and $R_{17}$, independently, is hydrogen, halo, alkyl, haloalkyl, hydroxy, or amino; each of $R_{10}$ and $R_{13}$, independently, is hydrogen, alkyl, or haloalkyl; n is 0; and A is alkylene.

5. The compound of claim 4 wherein each of $R_1$, $R_2$, $R_4$, $R_{4'}$, $R_7$, $R_8$, $R_9$, $R_{11}$, $R_{12}$, $R_{14}$, $R_{15}$, $R_{16}$, and $R_{17}$, independently, is hydrogen; and each of $R_{10}$ and $R_{13}$, independently, is alkyl; and A is alkylene.

6. The compound of claim 1, wherein the compound is

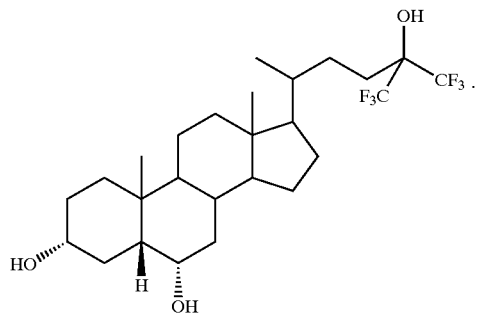

7. A pharmaceutical composition comprising:

an effective amount of a compound of the following formula:

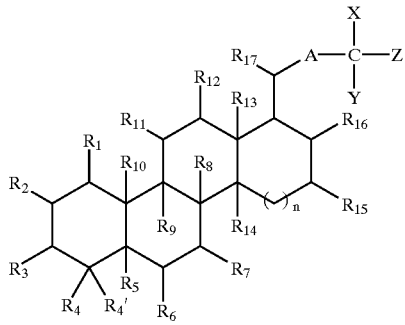

in which each of $R_1$, $R_2$, $R_4$, $R_{4'}$, $R_5$, $R_7$, $R_{11}$, $R_{12}$, $R_{15}$, $R_{16}$, and $R_{17}$, independently, is hydrogen, halo, alkyl, haloalkyl, hydroxy, amino, carboxyl, oxo, sulfonic acid, or ailcyl that is optionally inserted with —NH—, —N(alkyl)-, —O—, —S—, —SO—, —SO$_2$—, —O—SO$_2$—, —SO$_2$—O—, -SO$_3$—O—, —CO—, —CO—O—, —O—CO—, —CO—NR'—, or —NR'—CO—;

each of $R_3$ and $R_6$ is hydroxy;

each of $R_8$, $R_9$, $R_{10}$, $R_{13}$, and $R_{14}$, independently, is hydrogen, halo, alkyl, haloalkyl, hydroxyalkyl, alkoxy, hydroxy, or amino;

n is 0, 1, or 2;

A is alkylene, alkenylene, or alkynylene; and one of X, Y, and Z is —OR', and the other two are haloalkyl;

wherein R' is hydrogen; and a pharmaceutically acceptable carrier.

8. The composition of claim 7, wherein the compound is

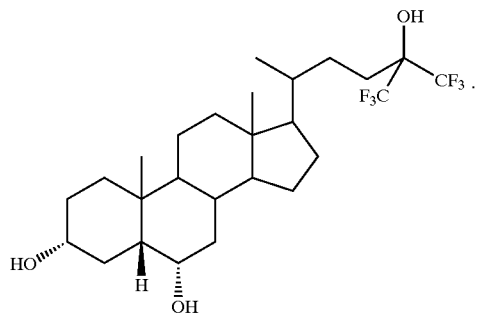

* * * * *